US00PP30425P3

(12) United States Plant Patent
Clark et al.

(10) Patent No.: US PP30,425 P3
(45) Date of Patent: Apr. 23, 2019

(54) GRAPE PLANT NAMED 'OPPORTUNITY'

(50) Latin Name: ***Vitis* L. hybrid**
Varietal Denomination: Opportunity

(71) Applicant: THE BOARD OF TRUSTEES OF THE UNIVERSITY OF ARKANSAS, Little Rock, AR (US)

(72) Inventors: John Reuben Clark, Fayetteville, AR (US); James N. Moore, Arlington, TX (US); Justin R. Morris, Springdale, AR (US); Renee Threlfall, Springdale, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 15/731,606

(22) Filed: Jul. 7, 2017

(65) Prior Publication Data

US 2019/0014699 P1 Jan. 10, 2019

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
See application file for complete search history.

(56) References Cited

U.S. PATENT DOCUMENTS

| | | | |
|---|---|---|---|
| PP13,309 | P2 | 12/2002 | Clark et al. |
| PP25,152 | P3 | 12/2014 | Clark et al. |
| PP25,696 | P3 | 7/2015 | Clark et al. |
| PP25,697 | P3 | 7/2015 | Clark et al. |
| PP25,726 | P3 | 7/2015 | Clark et al. |
| PP25,746 | P3 | 7/2015 | Clark et al. |

OTHER PUBLICATIONS

Clark, Moore, Morris and Threlfall, 'Opportunity' and 'Enchantment' Wine Grapes for the Mid-South of the United States, HortScience Aug. 2018 53:1208-1211.

Hightower, Grape, breeder travel the long road to a good Arkansas wine grape, University of Arkansas Cooperative Extension Service News, Nov. 10, 2016 available at https://www.uaex.edu/media-resources/news/november2016/11-10-2016-Ark-Long-Grape-Journey.aspx.

Mc Kee, New Wine Grape Varieties for the Mid-South University of Arkansas names Opportunity, a white grape, and Enchantment, a red grape, Sep. 30, 2016, Wines & Vines available at https://www.winesandvines.com/news/article/175263/New-Wine-Grape-Varieties-for-the-Mid-South.

*Primary Examiner* — Keith O. Robinson
(74) *Attorney, Agent, or Firm* — Andrus Intellectual Property Law LLP

(57) ABSTRACT

Description and specifications of a new and distinct wine grape cultivar which originated from a hand-pollinated cross of 'Cayuga White' (*Vitis labrusca* L. by *V. vinifera* L., developed by the New York State Agricultural Experiment Station, Geneva, N.Y.; female parent, non-patented) x A-1754 (non-patented, non-released breeding genotype; male parent). This new wine grape cultivar can be distinguished by its quality juice attributes for wine production with hardy and productive grapevines adapted to Arkansas and the Mid-South of the United States.

4 Drawing Sheets

Latin name: *Vitis* L. hybrid.
Varietal denomination: 'Opportunity'.

BACKGROUND

The new and distinct cultivar of white wine grape named 'Opportunity' is described herein. The new cultivar originated from a hand-pollinated cross of 'Cayuga White' (female parent; non-patented) and 'A-1754' (male parent; non-patented) made in 1987. The seedlings fruited in the summer of 1991 in a vineyard near Clarksville, Ark. and one was selected for its potential as a white wine grape for utilization in Arkansas and the Mid-South of the United States. The fruit grows in medium-large clusters, the vines have medium-high, but not excessive, vigor on hardy and productive plants and the wine has fruit-forward aromas and flavors.

SUMMARY OF THE INVENTION

The new and distinct cultivar of grapevine originated from a hand-pollinated cross of 'Cayuga White' (*Vitis labrusca* L. by *V. vinifera* L., developed by the New York State Agricultural Experiment Station, Geneva, N.Y.; female parent, non-patented) x 'A-1754' (non-patented, non-released breeding genotype; male parent) made in 1987 near Clarksville, Ark. The seeds resulting from this controlled hybridization were germinated in a greenhouse during the winter of 1987-88. Resulting seedlings were planted in the spring of 1988 in a vineyard near Clarksville, Ark. The seedlings fruited in the summer of 1991 and one seedling, designated Arkansas Selection 2245, was selected for its potential for processing for white wine along with good yields potential and adaptation to Arkansas and Mid-South of the United States.

During late 1991 and early 1992, the original plant selection was propagated asexually at the above-noted location, by rooting hardwood cuttings and a test planting of three vines was established. In all propagations, hardwood cuttings were used and the selection rooted readily from hardwood cuttings. All propagules (resulting plants) of the new cultivar have been observed to be true to type in that during all asexual multiplication, the vegetative and fruit characteristics of the original plant have been maintained. All vines planted from hardwood cutting propagation fruited in the third season of growth in the vineyard after planting.

Vines of the new cultivar have medium-high, but not excessive, vigor, with semi-procumbent growth habit intermediate between *V. vinifera* and *V. labrusca* hybrids. It has produced well as own-rooted plants in all testing and has not been evaluated on any rootstocks. Adaptation to the Arkansas test site is very good as winter injury and heat damage were not observed.

The health of the new cultivar is good. The new cultivar is moderately resistant to powdery mildew (*Erysiphe necator* Schw. (syns. *Uncinula necator* (Schw.) Burr., *E. tuckeri* Berk., *U. americana* Howe, and *U. spiralis* Berk. & Curt; anamorph *Oidium tuckeri* Berk.), downy mildew (*Plasmopora viticola* Berl. & Tomi.), and anthrancnose (*Elsinoe ampelina* (d. By.) Sher), but susceptible to black rot (*Guignardia bidwellii* (Ell.) V. & R.). It is also susceptible to Pierce's disease (*Xylella fastidiosa*). Fungal diseases can be controlled by the use of available fungicides.

The new cultivar average harvest date is 30 August. Yield averages 10.9 kg/vine with average cluster weight of 234.3 g. Clusters are very full with tightly attached berries. The berries are green in color at maturity and are medium in size (ca. 2.7 g). The berry has thin skin with a tannic characteristic. Fruit cracking was not observed during evaluation in summer rainfall near maturity.

The flavor attributes for the new cultivar are reflective of commercial standards for quality juice and wine. Soluble solids and titratable acidity concentration of the juice at fruit maturity averages 17.3% and 0.5%, respectively. Juice pH average is 3.5. The crush juice yield is 7.0 kg of grapes for 3.8 L of juice. 'Opportunity' wine has fruit-forward aromas and flavors for the production of green apple, honey-like, soft white wine with a balanced finish.

The new cultivar has been named 'Opportunity'.

BRIEF DESCRIPTION OF THE PHOTOGRAPHS

The accompanying photographs show typical specimens from 24 year-old vines grown near Clarksville, Ark. of the new cultivar in color as nearly true as it is reasonably possible to make in a color illustration of this character.

DETAILED DESCRIPTION OF THE NEW CULTIVAR

Figure 1:
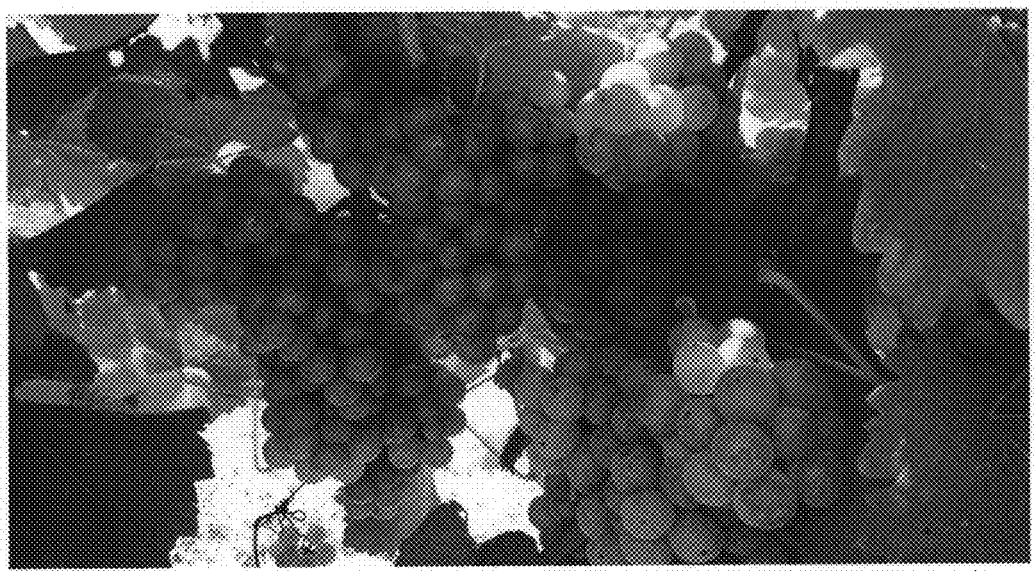
FIG. 1 is a photograph showing typical cluster of healthy fruit.
Figure 2:
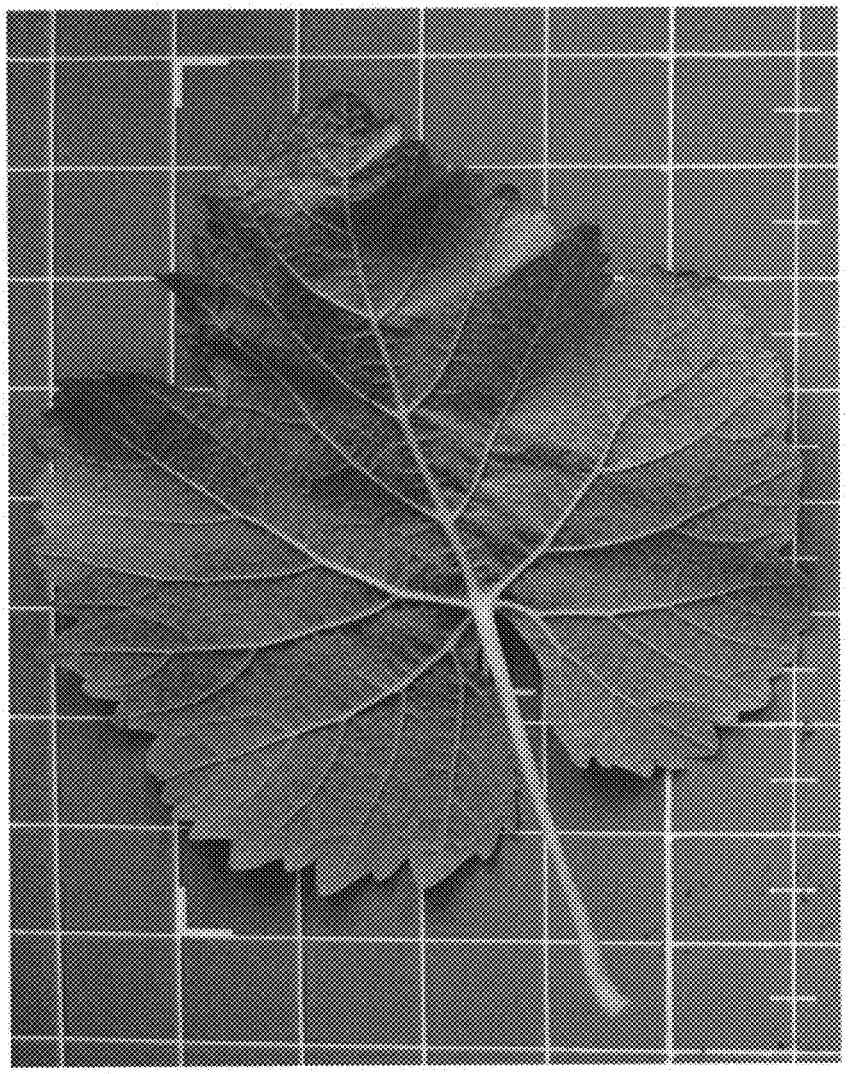
FIG. 2 is a photograph showing the leaf abaxial view.
Figure 3:
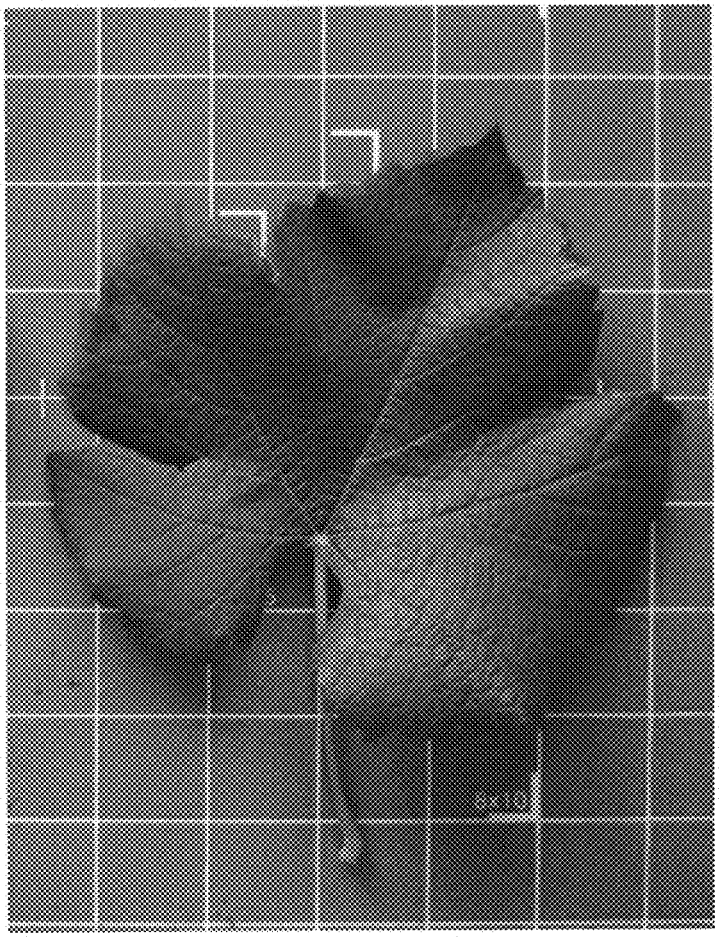
FIG. 3 is a photograph showing the leaf adaxial view.
Figure 4:
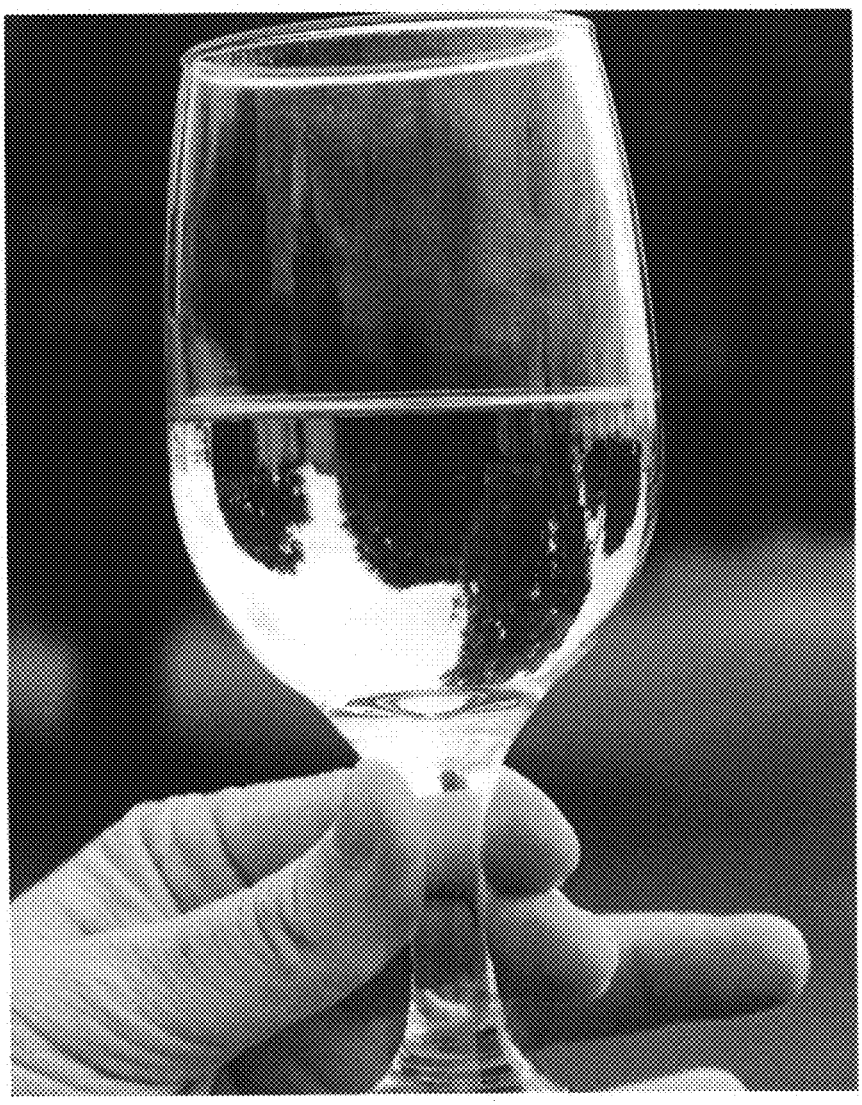
FIG. 4 is a photograph showing the wine.

'Opportunity' differs from its female parent 'Cayuga White' in that 'Opportunity' is less cold hardy and has more compact cluster fill. 'Opportunity' differs from its male parent 'A-1754' in that it yields more, is more consistently productive and has larger clusters.

The following is a detailed description of the botanical and pomological characteristics of the subject grapevine. Color data are presented in Royal Horticultural Society Colour Chart designations, 1986 version, second edition.

Where dimensions, sizes, colors and other characteristics are given, it is to be understood that such characteristics are approximations of averages set forth as accurately as practicable.

The descriptions reported herein are from specimens grown near Clarksville, Ark. Vines used for measurement were irrigated using trickle (drip) irrigation. Vines were fertilized annually in spring with N or complete fertilizers. Vines had a commercial fungicide program utilized during the growing season. No shoot or leaf thinning practices were conducted on the vines. The data collection was from vines that were 24 years old.

Vine:

*Size*.—Medium. Evaluation vines grown on a 5 ft high, single-wire trellis, bilateral cordon training system spaced 8 ft between vines occupy vine space fully.

*Growth vigor*.—Medium-high, but not excessive.

*Density of foliage*.—Medium.

*Productivity*.—Moderately productive. Yields average 24 lb/vine (10.9 kg/vine). The comparison wine grape cultivar 'Viognier' (not patented) had a yield of 24 lb/vine.

*Rootstock*.—None; vines tested were own-rooted vines.

*Cold hardiness*.—Hardy to −17° C. (1° F.); potentially more hardy as this was the coldest temperature experienced at the test site.

Shoots (current-season canes):

*Color of shoots*.—Sun exposed side: greyed-purple group 183-A; shaded side: yellow-green group 146-B; anthocyanin is present on shoot sides exposed to direct sunlight.

*Shoot attitude*.—Semi-procumbent.

Canes:

*Color of mature, dormant canes*.—Base: greyed-orange group 166-B; midpoint: greyed-orange group 166-C; terminal: greyed-orange group 166-D; anthocyanin not observed on mature canes at base, midpoint, or terminal.

*Texture of mature, dormant canes*.—Smooth.

*Length of mature, dormant canes*.—Average 1.2 m with range of 1.0 to 1.5 m.

*Diameter of mature, dormant canes*.—Base: 0.9 cm; midpoint: 0.6 cm; terminal: 0.4 cm.

*Internode length of mature, dormant canes*.—Base: 3.9 cm; midpoint: 9.1 cm; terminal: 2.9 cm.

*Lenticels*.—Not present on mature canes.

*Contour and shape of mature, dormant canes*.—Oblong. Canes mature to tips in the fall.

Trunk:

*Diameter at* 30 *cm above soil level*.—7.8 cm.

*Shape*.—Round.

*Trunk straps*.—Present.

*Surface texture*.—Rough.

*Color*.—Inner bark color: brown group 200-C; outer bark: black group 202-A.

Foliage:

*Leaves*.—

*Arrangement of mature leaves*.—Simple and alternate.

*Shape of mature leaves*.—Pentagonal.

*Number of lobes on mature leaves*.—3.

*Petiole sinus of mature leaves*.—Open, rounded/diamond.

*Venation of mature leaves*.—Palmate.

*Margin of mature leaves*.—Serrated with teeth shape of mature leaves: dentate and medium in size; teeth height: 4.0 mm; teeth width: 6.9 mm.

*Surface texture of mature leaves*.—Abaxial side: smooth; adaxial side: rough.

*Dimensions of mature leaves*.—Length: 13.0 cm; width: 16.7 cm; thickness: 0.04 cm.

*Pubescence on mature leaves*.—Abaxial side: none; adaxial side: moderate.

*Color of mature leaves*.—Base abaxial: green group 138-A; base adaxial: green group 138-B; midpoint abaxial: green group 138-A; midpoint adaxial: green group 138-B; terminal abaxial: green group 138-A; terminal adaxial: green group 138-B; no anthocyanin on upper or lower surfaces of leaves.

*Color of veins on mature leaves*.—Abaxial surface: yellow-green group 147-C; adaxial surface: yellow-green group 148-C; no anthocyanin on leaf veins.

*Autumn coloration of mature leaves*.—Abaxial surface: yellow-green group 153-B; adaxial surface: yellow-green group 153-D.

*Leaf pubescence on young leaves*.—Abaxial side: heavy; adaxial side: moderate.

*Color of young leaves*.—Base abaxial: yellow-green group 144-A; base adaxial: green group 138-B; midpoint abaxial: yellow-green group 144-A; midpoint adaxial: green group 138-B; terminal abaxial: yellow-green group 144-A; terminal adaxial: green group 138-B; anthocyanin presence slight to moderate on the back side of very young leaves.

*Vein color on young leaves*.—Abaxial side: yellow-green group 145-B; adaxial side: red-purple group 63-C.

Petioles:

*Color of mature petioles*.—Yellow-green group 146-C; anthocyanin not present on mature petioles.

*Dimensions of mature petioles*.—Length: 9.0 cm, diameter: 0.3 cm.

*Shape of mature petioles*.—Round.

*Pubescence on mature petioles*.—Light.

*Color of young petioles*.—Green group 143-C.

Tendrils: Found on the 6th node.

*Orientation*.—Opposite.

*Dimensions*.—Length: 20.4 cm; diameter: 0.2 cm.

*Texture*.—Smooth.

*Color of mature tendril*.—Greyed-orange group 177-A. Tendril forked and curled.

Buds:

*Number of buds on current, single-season cane*.—30.

*Dimensions of dormant buds*.—Length 0.4 cm; width: 0.3 cm.

*Shape of dormant buds*.—Triangular.

*Color of dormant buds*.—Greyed-orange group 165-A.

*Texture of dormant buds*.—Smooth; slightly rough where scales meet.

*Bud break*.—28 March.

Disease resistance: Moderately resistant to powdery mildew, downy mildew, and anthracnose, and susceptible to black rot. Susceptible to Pierce's disease. Other disease susceptibilities not known.

Flower:

*Fragrance*.—Heavy and distinct. Similar to *Vitis vinifera* vines.

*Sex*.—Hermaphrodite.

*Bloom dates*.—First bloom: 27 May; full bloom: 29 May.

*Flowers per cluster*.—275.

*Inflorescence dimensions*.—Length: 10.0 cm; diameter: 4.7 cm.

*Flower dimensions*.—Length: 0.2 cm; diameter: 0.3 cm.

*Flower longevity*.—Moderate to good.

*Flower shape*.—Roundish.

Stamens:

*Number*.—5 and erect.

*Color of filament*.—Yellow-orange group 16-A.

Pistil:

*Number*.—1.

*Length*.—0.2 cm.

*Color*.—Yellow-green group 146-B.

Pollen:

*Color*.—Yellow-orange group 16-A.

*Amount*.—Abundant.

Petal:

*Number*.—5 fused petals, form a tubular calyptra (flower cap).

*Color*.—Yellow-green group 146-C.

Sepal: None.

Pedicle:

*Dimensions*.—Length: 0.5 cm; diameter: 0.3 cm.

*Color*.—Green group 138-B.

Fruit/berries:

*Maturity*.—30 August.

*Berry shape and cross section*.—Round.

*Berry color*.—Skin: yellow-green 146-A; flesh: yellow-green 146-A; the berry skin has no anthocyanins present.

*Berry flesh color*.—Yellow-green group 142-D; the berry flesh has no anthocyanins present.

*Berry dimensions*.—Diameter at equator: 1.5 cm; diameter at base: 1.1 cm; diameter at apex: 1.1 cm; length: 1.6 cm.

*Berry weight*.—2.7 g. The comparison wine grape cultivar 'Viognier' had an average berry weight of 1.4 g/berry.

*Berry texture*.—Smooth.

*Firmness*.—Average for wine grape, softer than table grape. Rupture force to penetrate berry 21.6 N.

*Skin thickness*.—0.03 cm.

*Tenacity*.—Little, if any cracking in summer rainfall periods near harvest.

*Seeds*.—Yes. 2-3 fully developed/complete.

*Brush length*.—0.4 cm.

*Juiciness*.—Moderate to high.

*Attachment*.—Very good, difficult to remove grape from pedicel at maturity.

*Aroma*.—Present. Grassy, green apple.

*Flavor*.—Slight herbaceous, neutral.

Juice:

*Color*.—Greyed-orange group 163-C.

*Soluble solids*.—17.3%.

*Titratable acidity*.—0.5%.

*ph*.—3.5.

Seed:

*Number per berry*.—2.

*Seed dimensions*.—Length: 0.6 cm; width: 0.3 cm.

*Weight*.—0.03 g.

*Color*.—Top/bottom: greyed-orange group 165-B; sides: greyed-orange group 165-A.

*Shape*.—Obovate.

Cluster:

*Weight*.—234.3 g. The comparison wine grape cultivar 'Viognier' had a cluster weight of 141 g.

*Cluster dimensions*.—Length: 11.4 cm; width: 10.1 cm.

*Berries per cluster*.—96. The comparison wine grape cultivar 'Viognier' had a total of 102 berries/cluster.

*Cluster density*.—Dense to very dense.

*Clusters per vine*.—87. The comparison wine grape cultivar 'Viognier' had a total 80 clusters/vine.

*Clusters per shoot*.—2.6.

*Peduncle dimensions*.—Length: 0.8 cm; diameter: 0.2 cm.

*Peduncle color*.—Green group 140-C.

Wine quality:

*Flavor*.—Fruity.

*Aroma*.—Honey, fruit.

*Color*.—Clear, light gold.

*Finish*.—Medium, finish with balance.

*Overall quality*.—Comparable to established regional *Vitis* hybrid cultivars such as 'Seyval' or 'Verdelet'.

Use: Processing for white wine with improved vines particularly adapted for Arkansas and the Mid-South of the United States.

The cultivar: The most distinctive features of this cultivar are vines with medium-high vigor and consistent productivity, fruit with juice quality for white wine production, and plants with adaptation to Arkansas and the Mid-South of the United States.

We claim:

1. A new and distinct cultivar of grape plant named 'Opportunity', substantially as illustrated and described.

* * * * *